(12) United States Patent
Little, Jr.

(10) Patent No.: US 6,653,847 B2
(45) Date of Patent: *Nov. 25, 2003

(54) INTERFEROMETRIC LOCALIZATION OF IRREGULARITIES

(76) Inventor: Jack R. Little, Jr., 912 Holystone Dr., Baton Rouge, LA (US) 70808-5108

( * ) Notice: Subject to any disclaimer, the term of this patent is extended or adjusted under 35 U.S.C. 154(b) by 0 days.

This patent is subject to a terminal disclaimer.

(21) Appl. No.: 10/100,442

(22) Filed: Mar. 18, 2002

(65) Prior Publication Data

US 2003/0173977 A1 Sep. 18, 2003

Related U.S. Application Data

(63) Continuation of application No. 09/158,199, filed on Sep. 22, 1998, now Pat. No. 6,359,446.
(60) Provisional application No. 60/126,445, filed on Sep. 25, 1997.

(51) Int. Cl.[7] ............................................. G01R 27/00
(52) U.S. Cl. ..................................................... 324/637
(58) Field of Search ................................ 324/637, 631, 324/632, 639, 642, 644

(56) References Cited

U.S. PATENT DOCUMENTS

| | | | |
|---|---|---|---|
| 2,999,982 A | 9/1961 | Broussaud | 324/58.5 |
| 3,025,463 A | 3/1962 | Luoma et al. | 324/58.5 |
| 3,144,601 A | 8/1964 | Slabodsky | 324/58.5 |
| 3,271,668 A | 9/1966 | Haake et al. | 324/58.5 |
| 3,278,841 A | 10/1966 | Hanson et al. | 324/58.5 |
| 3,549,986 A | 12/1970 | Prine | 324/629 |
| 3,640,598 A | 2/1972 | Neeley et al. | 359/9 |
| 4,087,746 A | 5/1978 | Kanae | 324/58.5 A |
| 4,123,703 A | 10/1978 | Robinson | 324/58.5 B |
| 4,274,288 A | 6/1981 | Tittmann et al. | 73/602 |
| 4,344,030 A | 8/1982 | Anderson et al. | 324/58.5 B |
| 4,514,680 A | 4/1985 | Heikkila et al. | 324/639 |
| 4,520,308 A | 5/1985 | Rohde et al. | 324/58.5 R |
| 4,581,574 A | 4/1986 | Goodman et al. | 324/58 A |
| 4,634,963 A | 1/1987 | Lunden | 324/632 |
| 4,707,652 A | 11/1987 | Lowitz | 324/58.5 B |
| 4,754,214 A | 6/1988 | Bramanti et al. | 324/58 B |
| 4,845,356 A | 7/1989 | Baker | 250/225 |
| 4,891,573 A | 1/1990 | Kent | 324/629 |

(List continued on next page.)

FOREIGN PATENT DOCUMENTS

| | | |
|---|---|---|
| DE | 43 11 103 A1 | 10/1994 |
| JP | 61-274209 | 4/1986 |
| WO | WO 97/10514 | 3/1997 |

OTHER PUBLICATIONS

Bahr, A., "Microwave Nondestructive Testing Methods," pp. 1–85 (1982).

(List continued on next page.)

*Primary Examiner*—N. Le
*Assistant Examiner*—T. R. Sundaram
(74) *Attorney, Agent, or Firm*—John H. Runnels

(57) ABSTRACT

An apparatus and method for the nondestructive inspection of dielectric materials are disclosed. Monochromatic, phase coherent electromagnetic radiation, preferably in the 5–50 gigahertz frequency range (i.e., microwaves) impinges on the sample. In accordance with Snell's law, the microwaves are partly transmitted and partly reflected at each interface where the dielectric constant changes (e.g., where there are delaminations, cracks, holes, impurities, or other defects.) A portion of the reflected beam is combined with the signal reflected by the specimen being inspected. These two signals have the same frequency, but may differ in amplitude and phase. The signals combine to produce an interference pattern, a pattern that changes as the specimen changes, or as the position of the specimen changes relative to that of the detector.

13 Claims, 6 Drawing Sheets

U.S. PATENT DOCUMENTS

| | | | |
|---|---|---|---|
| 4,926,350 A | 5/1990 | Bechtel et al. | 702/36 |
| 5,103,181 A | 4/1992 | Gaisford et al. | 324/637 |
| 5,185,579 A | 2/1993 | Mertens et al. | 324/527 |
| 5,216,372 A | 6/1993 | Zoughi et al. | 324/644 |
| 5,233,306 A | 8/1993 | Misra | 324/601 |
| 5,376,889 A | 12/1994 | Milroy et al. | 324/644 |
| 5,384,543 A | 1/1995 | Bible et al. | 324/644 |
| 5,574,379 A | 11/1996 | Darling, Jr. | 324/642 |
| 5,748,002 A | 5/1998 | Scott et al. | 324/633 |
| 6,005,397 A | 12/1999 | Zoughi et al. | 324/644 |
| 6,359,446 B1 | 3/2002 | Little, Jr. | 324/637 |

OTHER PUBLICATIONS

Kurian, J. et al., "Microwave Non–Destructive Flaw/Defect Detection System for Non–Metallic Media Supported by Microprocessor–Based Instrumentation," J. Microwave-Power and Electromagnetic Energy, vol. 24, pp. 74–78 (1989).

Lucian, A.D. et al., "The Development of Microwave NDT Technology for the Inspection of Nonmetallic Materials and Composites," pp. 199–232 in Proceedings of the SixthSymposium on Nondestructive Evaluation of Aerospace and Weapons SystemsComponents and Materials (San Antonio, TX 1967).

M/A–COM Semiconductor Products, "Varactor Tuned Gunnplexer™ Transceiver 'Front End'," 21 unnumbered pages (1985).

Microwave Associates, "Varactor Tuned Gunn Oscillator Transceivers for Commercial Applications" (1977).

Various Authors, "The Microwave Gunnplexer™: An Introduction" (no date), 7 unnumbered pages.

Gutmann, R. J. et al., "Microwave Scanning Microscopy for Planar Structure Diagnostics," IEEE MTT–S Int'l Microwave Symposium Digest, Int'l Microwave Symposium, vol. 1, pp. 281–284 (Jun. 1987).

SCAN DISTANCE

TIME

INTERFEROMETRIC LOCALIZATION OF IRREGULARITIES

This is a continuation of prior application Ser. No. 09/158,199, filed Sep. 22, 1998, now U.S. Pat. No. 6,359,446; which claims the benefit of the Sep. 25, 1997 filing date of provisional application serial No. 60/126,445 under 35 U.S.C. §119(e); the entire disclosures of both of which are hereby incorporated by reference.

This invention pertains to an apparatus and method for the interferometric localization of irregularities.

There is an unfilled need for improved, nondestructive means to test dielectric materials for flaws, defects, and irregularities.

An example of this-unfilled need is that for improved, nondestructive means for inspecting rubber expansion joints. Although this invention has numerous applications and is by no means limited to the inspection of rubber expansion joints, that particular use will be described briefly because it played a significant role in inspiring the conception of this invention.

Most steam-cycle electric power plants employ rubber expansion joints between the condenser and the turbine. The expansion joints have multiple composite layers. Typical dimensions for such an expansion joint are in the neighborhood of 40 meters circumference, by 25 cm wide, by 1 cm thick. Under normal operating conditions, there is a vacuum on the inside of the joint, and 1 atm pressure on the outside. Thus when such a joint fails, it is prone to catastrophic failure.

A defect can begin, for example, when a small crack allows moisture inside the rubber. Moisture can then wick along the cords that form part of the composite. The moisture can cause the cord to deteriorate, which can lead to adjacent layers delaminating from one another. Defects such as these inside a joint are difficult to detect nondestructively through conventional means.

It is highly desirable that a testing procedure be nondestructive, and be usable whether the plant is running or idle. Furthermore, because the access space outside the joint can be as little as 7–10 cm, any portion of the detection machinery that must be in contact with the joint (or in the vicinity of the joint) should be small enough to fit into such a space.

If the joint were made of metal, then, well-established ultrasonic inspection techniques could be used. However, ultrasonic inspection cannot be used for rubber or soft plastic, because the polymers absorb nearly all sound energy, and reflect essentially none. The mesh or fabric of a composite material so highly scatters and disperses the ultrasonic waves that an extremely noisy reflection results. Eddy current measurements or magnetic measurements do not work well in rubber either, because rubber does not conduct electricity.

Neither is radiography particularly helpful. X-ray radiation is used to detect changes in bulk density. Under most operating conditions the most common flaw leading to failure is delamination. In a delamination failure, an essentially two-dimensional separation occurs between,adjacent component layers. This separation between layers does not typically result in a detectable change in local density, and is therefore not detectable in a radiograph.

The current state of the art for nondestructive testing of rubber parts is to use a Durometer, a needle that penetrates a portion of the rubber, and connects to a strain gauge. Durometers have poor practical utility, but they represent the best technology currently available for non-destructive testing of rubber joints.

An overview of microwave testing techniques may be found in A. Bahr, *Microwave Nondestructive Testing Methods* (1982).

Several microwave nondestructive testing techniques are disclosed in A. Lucian et al., "The Development of Microwave NDT Technology for the Inspection of Nonmetallic Materials and Composites," pp. 199–232 in *Proceedings of the Sixth Symposium on Nondestructive Evaluation of Aerospace and Weapons Systems Components and Materials* (San Antonio, Tex. 1967).

J. Kurian et al., "Microwave Non-Destructive Flaw/Defect Detection System for Non-Metallic Media Supported by Microprocessor-Based Instrumentation," *J. Microwave Power and Electromagnetic Energy*, vol. 24, pp. 74–78 (1989) discloses a method for detecting defects in a tire by measuring transmission of microwaves from a dipole transmitting antenna inside the tire, through the treads of the tire, with transmission detected by a linear array of detectors. Differential rates of transmission were correlated with changes in thickness or with defects.

C. Howell et al., *The Use of Low Cost Industrial AM-CW 'Microwave Distance Sensors' for Industrial Control Applications* (no date) discloses a microwave distance sensor to measure distances to an object from about 15 centimeters to about 6 meters away, by measuring the phase angle of a returned amplitude-modulated microwave signal reflected from the object.

U.S. Pat. No. 3,278,841 discloses a microwave flaw detection system, particularly for use with large, solid-propellant rocket motors. Microwaves were transmitted from inside the propellant, reflected off a metal casing, and detected by a receiver displaced from the microwave transmitter. Irregularities in the strength of the received signal were correlated with cracks or other flaws in the propellant.

U.S. Pat. No. 4,520,308 discloses a system for measuring the thickness of a. dielectric material by measuring the phase shift of microwaves transmitted along a microwave strip line conductor that is adjacent to the material whose thickness is being measured. See also U.S. Pat. No. 4,123,703.

U.S. Pat. No. 2,999,982 discloses a Doppler-effect-based method for microwave detection of homogeneity defects in compact materials such as polished glass. Relatively high speeds of scanning were used to generate the desired Doppler effect. In the one example given, the relative speed of the glass versus the detector was 650 centimeters per second.

U.S. Pat. No. 3,144,601 discloses a method for microwave detection of non-homogeneous zones in non-conducting materials such as glass sheets and plates. Detection was performed by simple measurement of the echoes of the reflected microwaves; by measuring losses in intensity following transmission through the object; or by mixing incident and reflected waves to create beats, particularly when the material being examined was traveling (i.e., detecting Doppler shifts in the frequency of the reflected microwaves).

U.S. Pat. No. 3,271,668 discloses the use of microwaves to measure the rate of progressive attrition from a surface of a body of a solid dielectric material; for example, measuring the burning profile in a solid rocket motor. Microwaves were transmitted through the fuel (or other material), the surface of which reflected some of the microwaves back to a detector. The relative phase of incident and reflected microwaves varied as the distance from the microwave transmitter to the surface of the burning fuel changed, allowing the distance to the surface of the fuel to be determined as a function of time.

U.S. Pat. No. 4,707,652 discloses a technique for detecting impurities in a bulk material by measuring changes in the scattering of microwave radiation incident on the bulk material.

U.S. Pat. No. 4,514,680 discloses a method for detecting knots in lumber, by transmitting microwaves through the lumber from two sources of the same intensity, but with a 180° phase shift. Transmitted microwaves are detected on the opposite side of the lumber. If the lumber is knot-free, there is a null in the microwave field at the detectors, but if a knot is present the phase and amplitude of microwave radiation at the detectors are altered.

U.S. Pat. No. 4,581,574 discloses a method for determining the average dielectric constant of a dielectric material having a conductive surface, by transmitting microwaves from two transducers into a sheet of the material, and making measurements of the energies of reflected microwaves. By measuring average dielectric constants along a plurality of paths in the plane of the sheet, locations of variations within the sheet may be identified.

U.S. Pat. No. 4,274,288 discloses an acoustic, interferometric method for measuring the depth of a surface flaw such as a crack.

U.S. Pat. No. 4,087,746 discloses a method for determining optical anisotropy in a dielectric material by measuring changes in the polarization of microwaves transmitted through the material.

A novel apparatus and method have been discovered for the nondestructive inspection of dielectric materials. Monochromatic, phase coherent electromagnetic radiation, preferably in the 5–50 gigahertz frequency range (i.e., microwave radiation) impinges on the sample. In accordance with Snell's law, the microwaves are partly transmitted and partly reflected at each interface where the dielectric constant changes (e.g., where there are delaminations, cracks, holes, impurities, or other defects.)

A portion of the transmitted beam is combined with the signal reflected by the specimen being inspected. These two signals have the same frequency, but may differ in amplitude and phase. The signals combine to produce an interference pattern, a pattern that changes as the specimen changes, or as the position of the specimen changes relative to that of the detector. Appropriate processing of the interference signal can greatly improve the signal-to-noise ratio. The detector may be scanned relative to the specimen at any desired speed, and the scanning speed need not be uniform. The novel detection technique is not based on Doppler-shifts in frequency, which result from motion, but rather is based on interference between reflected and reference microwaves having substantially the same frequency, where the interference is caused by changes in location (independent of motion per se).

The novel technique can detect cracks, voids, foreign material inclusions (e.g., water or oil), thickness changes, delaminations, changes in dielectric constant (which in rubber may, for example, indicate. aging), and other defects in essentially any dielectric materials. Different types of defects have distinguishable characteristics. The technique can also be successfully used on composite materials containing conductive components, but whose construction makes them overall nonconductors—for example, carbon fiber composites.

Substances such as fiberglass that produce noisy reflection patterns in prior ultrasonic techniques may be inspected at low noise levels with the novel microwave technique. The novel technique readily detects many common defects in fiberglass.

The novel method and apparatus have been successfully tested in a prototype embodiment. The microwave transmitter/detector was small, and readily suited for use in environments in which access space may be limited.

Figure 1:
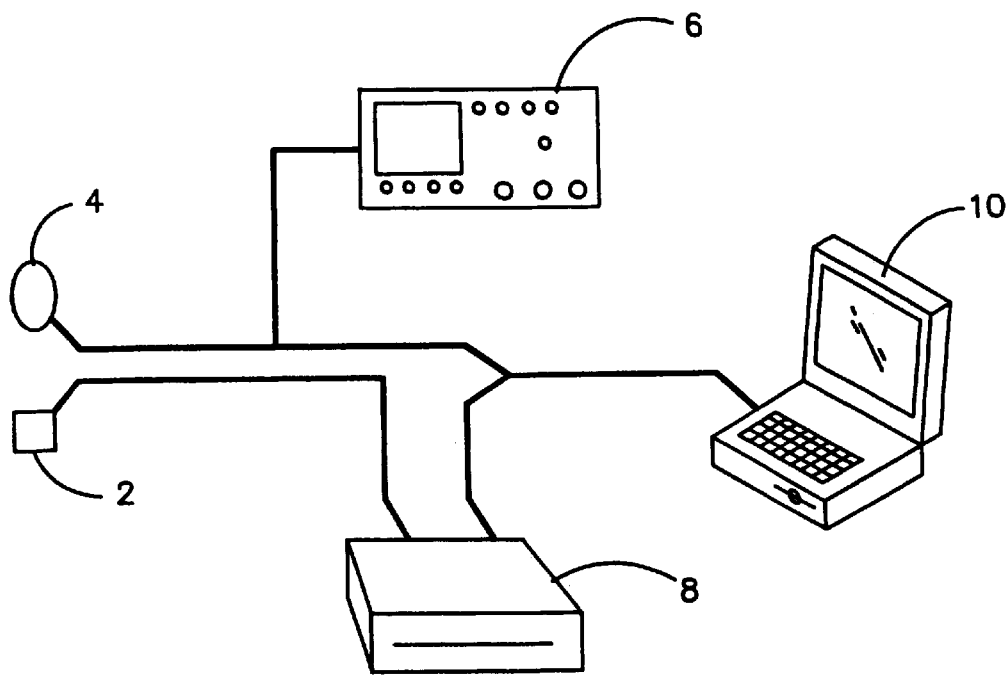
FIG. 1 depicts a schematic diagram of one embodiment of a defect measurement device in accordance with the present invention.

A schematic diagram of one embodiment of the apparatus is illustrated in FIG. 1. Transducer 2 and optical encoder 4 received regulated DC power from power supply 6. Signals from transducer 2 and (optionally) optical encoder 4 were transmitted to amplifier 8, which amplified and conditioned the signals before sending them to computer 10. In addition to the elements ordinarily found in a modern personal computer, computer 10 also included a 16-bit, analog-to-digital data acquisition system, and an input board for input wiring terminations. The computer was programmed with software whose function is described below.

The Transducer

A preferred transducer 2 was the Gunnplexer™ transducer (M/A-COM Semiconductor Products, Burlington, Mass.), a small and efficient microwave generator based on a gallium arsenide junction diode. See, e.g., B. Hale (ed.), *The 1989 ARRL Handbook for the Radio Amateur*, pp. 32–57 & 32–5.8 (66th ed., 1988); *The Microwave Gunnplexer™: An Introduction* (various authors, no date); M/A-COM Semiconductor Products, *Varactor Tuned Gunnplexer™ Transceiver "Front End"* (1985); Microwave Associates, *Varactor Tuned Gunn Oscillator Transceivers for Commercial Applications* (1977). The transducers that were used in prototype embodiments of the invention were tunable 10 or 25 gigahertz Gunnplexer™ transceivers (frequencies could be higher or lower if desired, e.g., 5–50 GHz). The transceiver could be used with or without a horn waveguide. The detector was a microwave frequency diode incorporated as part of the Gunnplexer™ assembly. The detector diode was located inside the out-going radiation beam, between the aperture and the front surface of the transducer housing. The Gunnplexer™ transducer is frequency stable, and requires only a 5–10 Volt DC power supply to produce the desired microwave output energies. It was mounted in a hand-held housing, and was connected to signal processing electronics and data acquisition hardware via a multiple conductor coaxial cable.

The hand-held unit also contained an optical encoder mounted to a wheel for measuring the position or displacement of the transducer. The optical encoder output fed to one input channel of the PCMCIA-based data acquisition system, which was located in the inspection system portable ("notebook") computer.

Signal Processing and Power Supply

The detection diode was located at a fixed position within the path of the outgoing microwave beam, so that the output signal had a constant amplitude and frequency. Microwaves radiated from the transducer to the specimen being tested. Each time the beam came to an interface between materials of different dielectric constants (e.g., the interface between the air and the specimen, or the interface between the bulk specimen and a flaw within), a portion of the energy in the beam was transmitted, and a portion reflected. The portion reflected depended on the angle of incidence, the differential in the dielectric constants between the materials (which is related to the index of refraction), the surface texture,.and other factors. Some of the reflected portion of the interrogating beam returned to the transducer, where it was detected by the detector diode. The reflected signal and the transmitted signal were of identical frequency, but (in general) differed in both amplitude and phase. These two simple sinusoids added together (were mixed) at the detecting diode, which produced a DC voltage that changed as the sample (or portion of sample) under inspection changed. In most specimens there are many interfaces, producing many reflected signals. However, regardless of the complexity of the reflected signal, the detector diode output produced a constant DC voltage when the position of the transducer relative to the specimen was held constant. In the following discussion this constant DC voltage will be referred to as the "SIGNAL."

The SIGNAL was transferred to signal processing electronics via coaxial cable. The observed SIGNAL was typically on the order of 1–100 millivolts at the input of the signal processing electronics. The SIGNAL was converted from analog to digital form in the PCMCIA DAS described earlier. The analog SIGNAL was digitized in 12 bits, resulting in a resolution of 1 part in 4096. The PCMCIA DAS used in the prototype had a fixed analog input span from −5 to +5 VDC. Routing the SIGNAL directly to the PCMCIA DAS would have resulted in a SIGNAL resolution of 2.44 mV, which would not allow the resolution of extremely small defects that the intrinsic frequency stability and low noise of the transducer would otherwise permit. A 20-gain amplifier was therefore included in the signal processing, prior to the A-to-D converter. The amplifier improved the SIGNAL resolution to 0.122 mV. A refined prototype embodiment, using a 16-bit PCMCIA DAS with an analog output span from −1.25 V to +1.25 V in conjunction with the amplifier, had a resolution on the order of 1.9 pV.

The PCMCIA DAS used supported seven analog input channels, and four digital channels that could be configured as either input or output channels. One analog channel was used to input the amplified SIGNAL, and another was used for input from the optical encoder.

The optical encoder was configured to indicate changes in the displacement of the transducer as the transducer moved across the test specimen. Measuring SIGNAL as a function of displacement is sometimes referred to here as inspection in the "displacement domain." The displacement input could optionally be disabled by software controls in situations where continuous contact of the encoder roller with a suitable surface could not be ensured. Disabling the displacement input can be helpful when performing inspections on specimens with complex shapes, or when access to the specimen is difficult. Inspection with the displacement input disabled is sometimes referred to as inspection in the "time domain." When care is taken to scan at a constant velocity, scanning in the time domain is equivalent to scanning in the displacement domain, and essentially the same signal processing techniques may be used to enhance the signal-to-noise ratio.

The power supply comprised a regulated, low-voltage power supply for the microwave generator between 5 and 12 VDC, capable of approximately 750 milliamps. The 5–12 volts were delivered to the transducer housing, where power was delivered to the Gunnplexer™ transducer. A 9-volt battery and a regulated 5-volt DC power supply were used for the optical encoder. Power for the signal processing amplifier was provided by a 9 volt battery, which provided many hours of service due to the extremely high input impedance of the DAS used. Power for the scanning system DAS and the computer were provided by the notebook computer itself.

Figure 11:
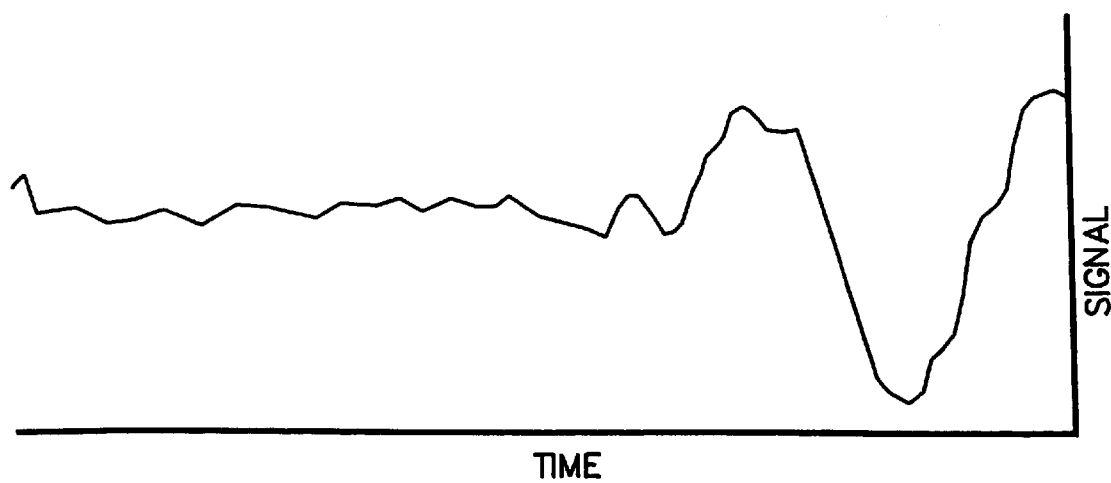
FIG. 11 depicts a scan of an artificial defect in an expansion joint.

FIG. 11 depicts an experimental scan of a defect in an expansion joint of the type commonly used in steam-cycle electric power plants, a Maryland Flexcon™ "dog bone" expansion joint that was 28 inches long, 9⅜ inch wide, and ⅝ inch thick. In the joint an artificial defect was created that was ¼ inch wide, 2 inches long, and 3/16 inch deep. This defect simulated the size of defects commonly suffered by such joints while in service. The scan depicted in FIG. 11 was made normal to the surface in the displacement domain, with a scan 17.69 inches long. The artificial defect was on the opposite side of the joint from the scanner, and was located 14.78 inches into the scan. No special signal analysis was required to extract the defect signal from the noise. The broad, symmetric waveform was characteristic of a thickness change resulting from removal of rubber in the joint. This type of damage (removal of rubber from an expansion joint) commonly occurs after a period of service, and may be caused, for example, by mechanical wear or gouging of the joint by loose or damaged internal hardware. While hardening and other age-related degradation may be detected by inspection with a Durometer, the type of internal damage that was detected here—damage that can lead to catastrophic failure—cannot be detected with previously available technologies without first obtaining access to the inside of the joint, requiring expensive unit outage. The current invention provides a previously unavailable solution to this problem. Internal defects may now be detected without shutting down the unit.

Signal Analysis

The novel technique is based on the principle that a change in the reflectivity of a specimen generally indicates the presence of a flaw. This "different is bad" approach. can be used to identify changes in thickness, foreign material inclusions, cracks, and other defects. As the location of the probe changed relative to the specimen, a defect was seen first moving into, and then moving out of the microwave beam. Inhomogeneities (defects) acted as microwave reflectors that moved relative to the transducer. In a preferred technique, the transducer was held at an angle such that the beam faced slightly forward during scanning. Depending on the scanning angle used, some fraction of the change in displacement was along the axis of microwave propagation. As reflectors "moved" toward or away from the transducer, a characteristic sinusoid was produced for each reflector as discrete signal samples were taken at discrete distances. Axial "motion" of the reflector produced peaks and troughs as the reflector moved through wavelengths of the interrogating radiation. (For example, at 10 GHz the wavelength is about 2.998 cm or 1.180 inches). Two cycles were observed per wavelength of axial displacement change.

During displacement domain scanning, information was simultaneously gathered for discrete values of both the SIGNAL and the location. These data were processed by the computer in real time (or pseudo-real time) to yield a plot of SIGNAL versus distance. In displacement domain scanning, a real defect produced a sinusoidal SIGNAL. The observed sinusoid had a spatial wavelength dependent on the frequency of the interrogating beam and on the scanning angle, but independent of scanning velocity. Spurious indications caused by variations in the distance between transducer and specimen ("lift-off"), wobbling of the transducer, and other small scanning inconsistencies produced noise, but the noise was not (in general) at the characteristic spatial wavelength. A Fourier transform or fast Fourier transform (FFT) of the SIGNAL produced the "spatial frequency domain." This Fourier transform is preferably made in real time or pseudo-real time.

Because real defects generated peaks at a characteristic spot in the spatial frequency spectrum, and because the power at this spatial frequency was a function of the size of the defect, the spatial frequency spectrum provided information on both the position and size of defects. By contrast, spurious SIGNAL variation (i.e., noise) was spread across the spectrum of the spatial frequency domain. Rejecting signals at other spatial frequencies greatly enhanced the signal-to-noise ratio, thereby improving sensitivity and the ability to automate scanning by subtracting the noise baseline from the spatial frequency spectrum.

Another method has been discovered for further improving the signal-to-noise ratio. By taking the first derivative of the Fourier transform with respect to either time or displacement, depending on the scanning domain used (with a bandpass consonant with the wavelength of the interrogating radiation, the angle of incident radiation, and, for time-domain scanning, the speed that the detector moves), the signal-to-noise ratio may be greatly enhanced. Using the time (or displacement) derivative of the FFT enhances the ability to distinguish signal from noise, even where the level or quality of noise varies during a scan, or where the direction of the scan changes during a single scan.

Although in principle this technique for improving the signal-to-noise ratio should work for either time domain or displacement domain measurements, in practice it works better with displacement domain measurements. It is often difficult to make scans at truly constant velocities under working conditions in the field. If the velocity varies during time-domain scanning, information pertaining to the presence and magnitude of a defect "leaks" to adjacent regions of the FFT, significantly reducing the signal-to-noise enhancement. However, using an optical encoder, and sampling the signal channel only when pulses are detected from the optical encoder channel (i.e., at evenly-spaced displacements), even under working conditions in the field displacement domain data can be collected with a high degree of precision. If a defect is present, then an FFT of the displacement domain measurements produces a power spectrum having a peak whose spatial frequency is characteristic of the particular device used (depending on factors such as interrogating frequency, scan angle, and optical encoder spatial resolution), but independent of the velocity or variations in the velocity of the scan.

Figure 5:
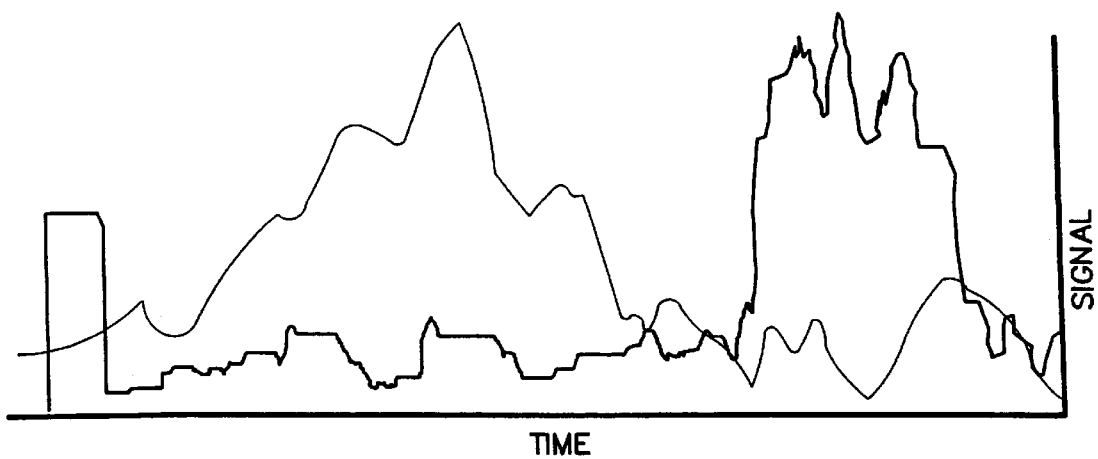
FIG. 5 depicts a scan of a test specimen of polymethylmethacrylate with a hole drilled into the bottom surface.

In one experiment, an 11 inch by 18 inch test specimen of polymethylmethacrylate (PMMA, or Plexiglas™) approximately 2 inches thick had a hole drilled into it about 0.25 inch in diameter, extending from the bottom surface (the side away from the detector) about halfway up through the PMMA. The defect was positioned so that it passed through the interrogating beam about 85% of the way through the scan. Scanning was performed in the time domain, with a constant scanning velocity. The transducer was pointed in a direction about 15° forward of normal. Results are shown in FIG. 5. The lighter curve depicts the raw data, and the solid line depicts the first derivative of an FFT of the raw data, with a bandpass of 20 to 30 Hertz. When scanning is performed in the time domain, the FFT operation yields the frequency or $1/\lambda$ domain. The bandpass was chosen to contain the apparent wavelength of the interrogating radiation along the axis of scan motion. (This "apparent wavelength" differs from the actual wavelength by a factor approximately equal to the cosecant of the scanning angle.) The defect clearly appears as the large, broad peak on the right part of the heavier curve in FIG. 5. (The plateau on the left in FIG. 5 is an artifact.)

Figure 6:
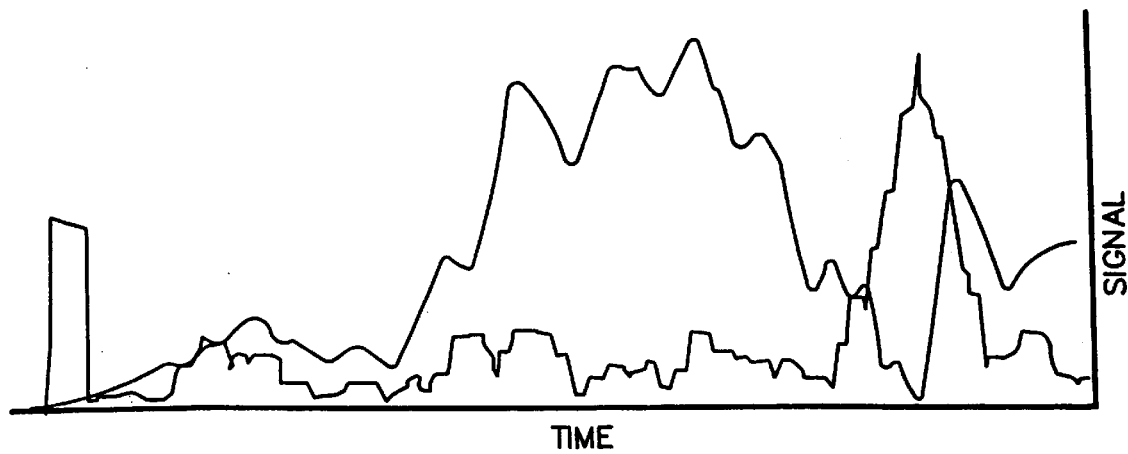
FIG. 6 depicts a slower scan of the same specimen tested in FIG. 5.

FIG. 6 depicts a slower scan of the same specimen tested in FIG. 5. Despite the differing speeds of the scans, and the very different appearance of the raw data, the first derivative of the FFT picked up the same defect towards the right of the figure. This similar performance under different operating conditions demonstrates the reproducibility and consistency of the novel method.

Figure 7:
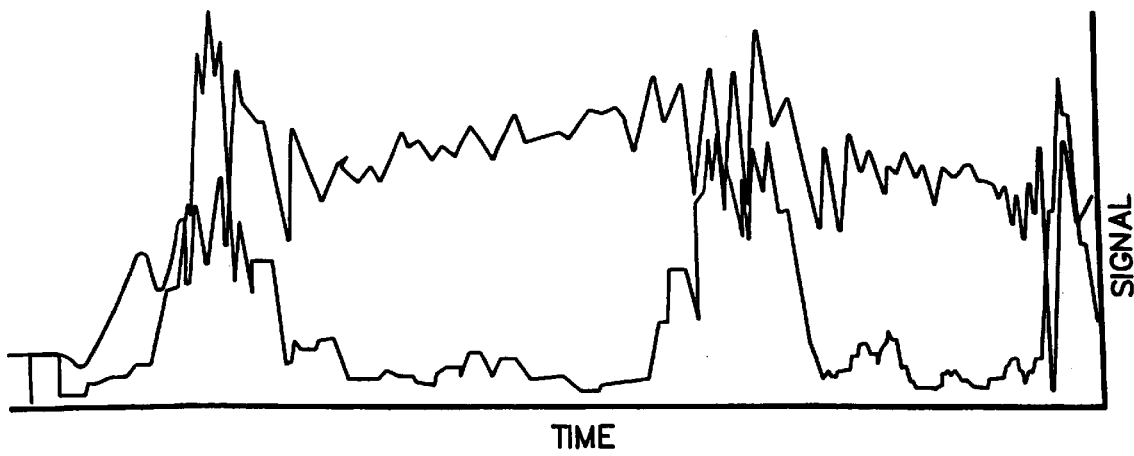
FIG. 7 depicts a scan of a particle board into which three wood screws had been placed.

FIG. 7 depicts a scan of a particle board table top about ⅝ inch thick into which three 0.25 inch long wood screws had been placed, approximately 9 inches apart from one another, into the surface on the far side of the particle board from the transducer. The screws protruded less than 0.25 inch into the particle board. Again, the three defects clearly appear in the first derivative of FFT plot (the lower curve). In this instance, the scan was performed with the transducer normal to the specimen surface. The interference patterns resulted from the fact that the wavefronts were spherical, and crossed the defects as the transducer moved. Had planar wavefronts been used instead, then lateral motion of the transducer normal to the surface would have not have produced an interference pattern from the defects, as the defects would not have passed through wavefronts as the transducer moved.

Depth Measurements

Figure 2:
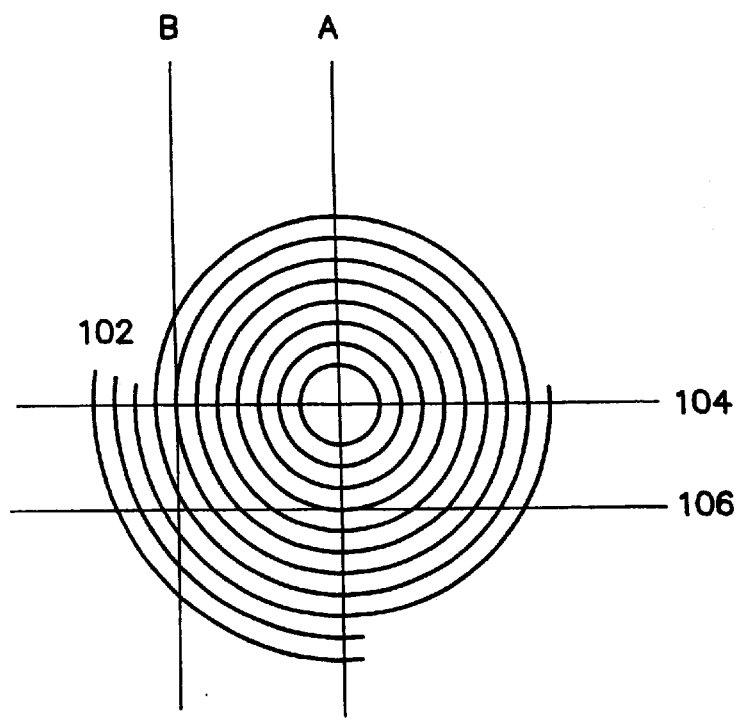
FIG. 2 illustrates how the number of spherical wavefronts from interrogating radiation crossed during scanning varies as a function of depth.
Figure 4A:
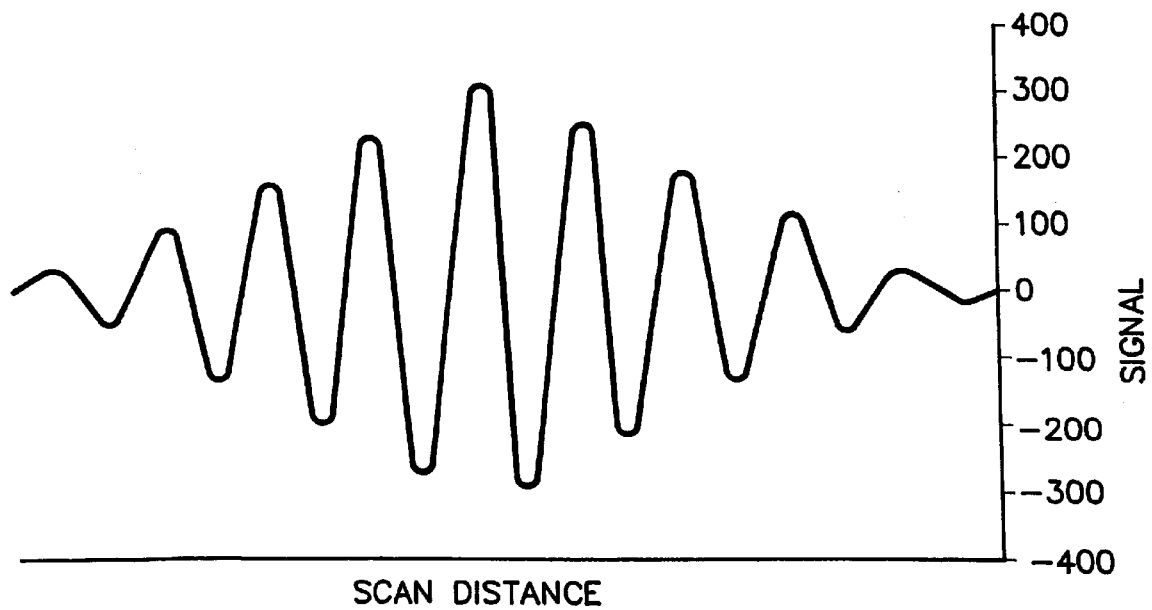
FIGS. 4(a) and 4(b) depict scans of a deeper defect, and a shallower defect, respectively.
Figure 4B:
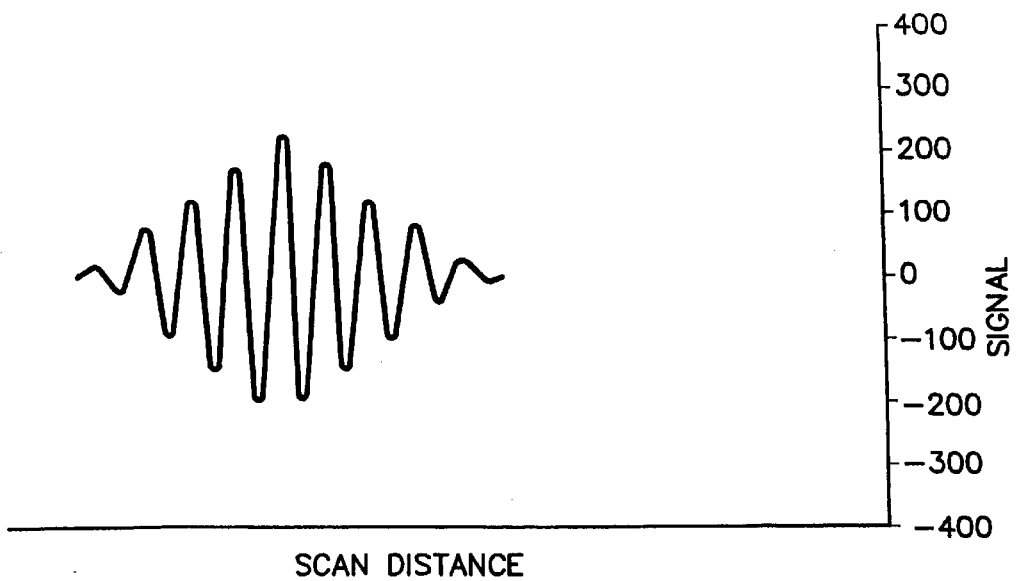

When a spherical wavefront is used (e.g., diffracting the microwaves through a hole whose diameter is small compared to the wavelength), the depth of a defect may be measured. As illustrated in FIG. 2, when the microwave source (not illustrated, but positioned at the center of the concentric waves depicted) moves, the number of wavefronts 102 crossed varies as a function of depth. During a scan over a fixed distance on the surface with a spherical wavefront, a greater number of wavefronts will cross a defect nearer the surface than one that is deeper. For example, as the detector moves from point A to point B, 7 wavefronts will cross a point on the surface 104, while only 4 wavefronts will cross a point at depth 106. Thus the spatial frequency of the detected beats indicates the depth of the defect responsible for the beats. FIGS. 4(a) and 4(b) depict idealized displacement domain scans of otherwise similar defects, in which the defect of FIG. 4(a) is deeper and the defect of FIG. 4(b) is shallower. The longer wavelength (lower spatial frequency) of FIG. 4(a) is characteristic of a deeper defect.

Figure 3:
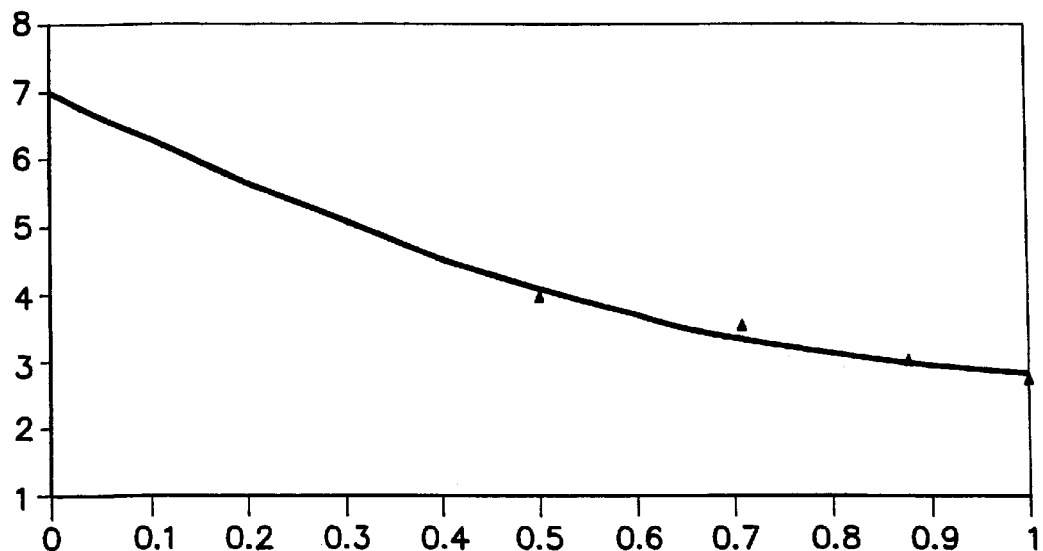
FIG. 3 illustrates a calibration of the number of wavefronts crossed by defects during scanning as a function of depth.

A calibration curve of the relationship between depth and frequency may be determined either theoretically from trigonometric relationships, or (preferably) by calibration by measurements with actual test defects at varying depths. The wavelength of interrogating radiation will impose a practical limit on this method of measuring depth; a limit that can be extended somewhat by increasing the wavelength of the interrogating radiation. An example is illustrated in FIG. 3, depicting the number of wavefronts crossed by defects as a function of depth, for the system illustrated in FIG. 2. The vertical axis shows the number of wavelengths crossed, and the horizontal axis shows the depth of the defect in the specimen, as a fraction of the wavelength of the interrogating radiation. The triangles depict discrete data points taken graphically from FIG. 2, and the curve depicts the best quadratic fit to the measured points, with $r^2$=0.998.

Figure 8:
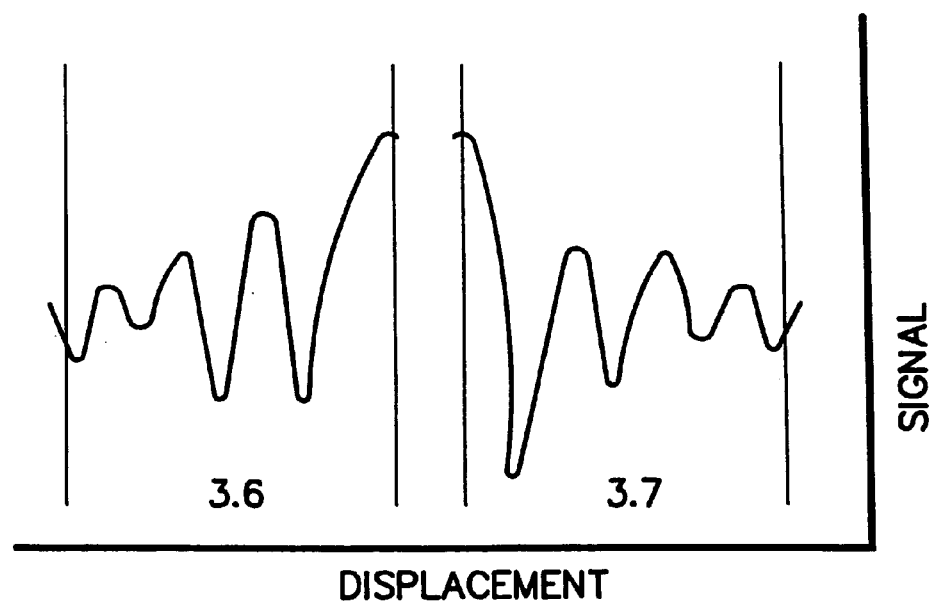
FIGS. 8 and 9 depict a displacement domain scan over one of the screws in the particle board of FIG. 7, with the scan taken from different distances from the screw.
Figure 9:
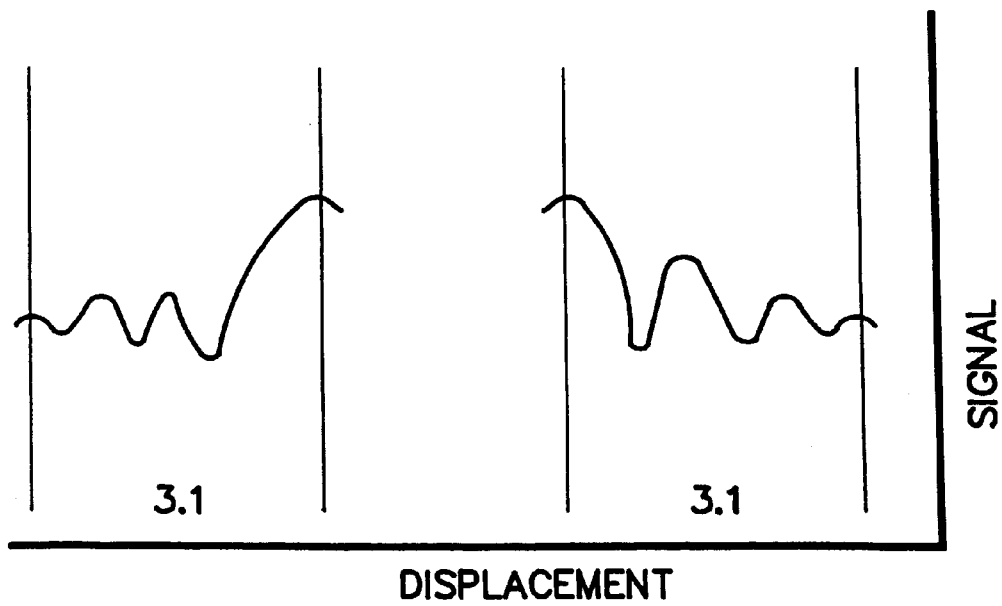
Figure 10:
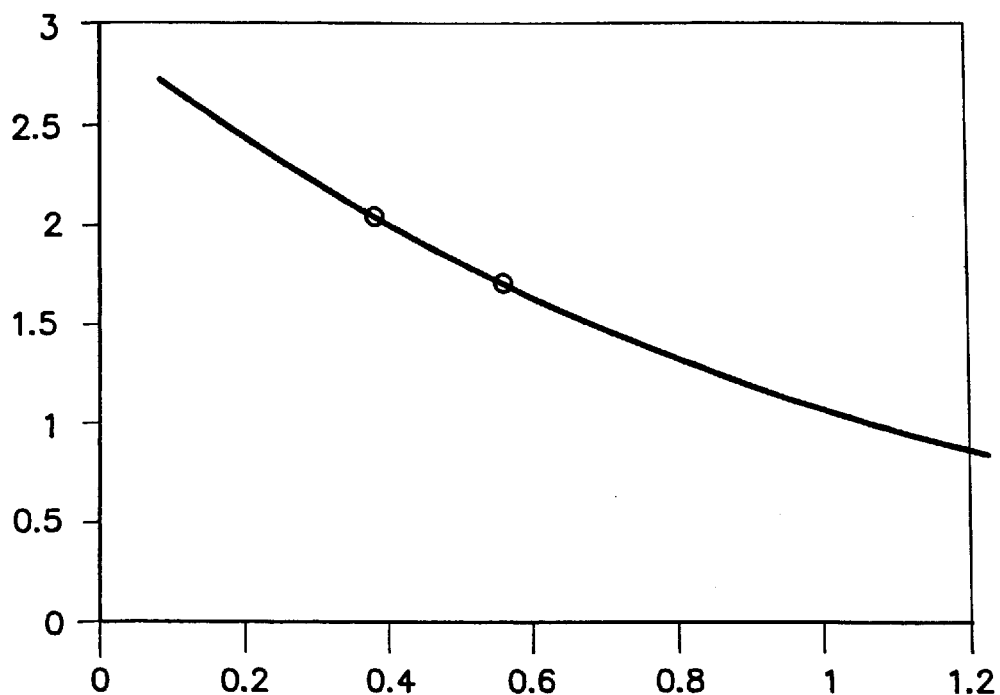
FIG. 10. depicts a preliminary calibration curve of depth versus spatial frequency of the interference pattern.

Experimental data demonstrating this method of determining defect thickness are illustrated in FIGS. 8 and 9. Each of FIGS. 8 and 9 depicts a displacement domain scan over just one of the screws in the ⅝ inch thick particle board described above in connection with FIG. 7, with the screws protruding approximately 0.25 inch into the bottom side (the side away from the scanner). The displacement domain scan was taken normal to the surface, over a total scanning distance of approximately 8.4 inches. In FIG. 8, the wave packet exhibited a spatial frequency of 2.033 cycles per scan inch. In FIG. 9, an additional 3/16 inch of thickness was added to the particle board's ⅝ inch thickness (for a total thickness of 13/16 inch) by adding a layer of corrugated cardboard. With the extra thickness, the wave packet exhibited the different spatial frequency of 1.703 cycles per inch. By repeating such measurements with "control" defects at differing depths, a calibration curve may be created for the depth of a feature as a function of the spatial frequency of the observed wave packet. A preliminary calibration curve, based on just these two points, is depicted in FIG. 10. In FIG. 10, the horizontal position is the depth of the near end of the. defect, in inches. The vertical position is the spatial frequency of the interference pattern, in cycles per inch. The accuracy of the calibration curve could be improved with additional experimental data points from defects of known depth.

The complete disclosures of all references cited in this specification are hereby incorporated by reference. In the event of an otherwise irreconcilable conflict, however, the present specification shall control.

I claim:

1. A method for detecting the presence of an irregularity in a bulk dielectric material, comprising the steps of:
   (a) generating microwaves that are of substantially constant frequency, between 5 and 50 gigahertz;
   (b) directing a first portion of the generated microwaves to impinge onto the material; whereby the impinging microwaves are partially transmitted and partially reflected when the impinging microwaves impinge on an irregularity within the material that is characterized by at least one interface between different dielectric constants; whereby the wavelength of the reflected microwaves is substantially the same as the wavelength of the impinging microwaves; and wherein the reflected microwaves may have an amplitude that differs from the amplitude of the impinging microwaves, or the reflected microwaves may have a phase that differs from the phase of the impinging microwaves, or both;
   (c) mixing the reflected microwaves with a second portion of the generated microwaves to produce an interference pattern that is a function of the position, size, shape, and composition of any irregularities in the material; and
   (d) inferring the position of at least one interface between different dielectric constants from the interference pattern.

2. A method as recited in claim 1, additionally comprising the steps of:
   (a) impinging microwaves onto the material at a plurality of different positions relative to the surface of the material; wherein the direction of the impinging microwaves in at least some of the positions is other than normal to the surface of the material; whereby the interference pattern that is attributable to an irregularity in the material changes in a sinusoidal or attenuated sinusoidal pattern as the position of the impinging microwaves changes relative to the irregularity, wherein the spatial wavelength of the sinusoidal pattern is a function of the angle between the direction of the impinging microwaves and a direction normal to the surface of the material; and
   (b) distinguishing features in the interference pattern attributable to irregularities in the material from features in the interference pattern attributable to sources of noise.

3. A method as recited in claim 2, additionally comprising the step of filtering from the interference pattern any features that do not have a sinusoidal or attenuated sinusoidal pattern with a wavelength substantially equal to the wavelength that is characteristic of the angle between the direction of the impinging microwaves and a direction normal to the surface of the material; whereby the signal-to-noise ratio of the interference pattern is enhanced.

4. A method as recited in claim 3, wherein said filtering is performed by taking a Fourier transform of the interference pattern, and rejecting components of the Fourier transform that do not correspond to a wavelength substantially equal to the wavelength that is characteristic of the angle between the direction of the impinging microwaves and a direction normal to the surface of the material.

5. A method as recited in claim 4, additionally comprising the step of generating the first derivative of the Fourier transform with respect to time or displacement, whereby the first derivative enhances the signal-to-noise ratio of the inferred information concerning the position of irregularities in the material.

6. A method as recited in claim 1, additionally comprising the steps of:
   (a) impinging microwaves onto the material at a plurality of different positions relative to the surface of the material; wherein the microwaves impinged onto the material have a substantially spherical wavefront; whereby the interference pattern that is attributable to an irregularity in the material changes in a sinusoidal or attenuated sinusoidal pattern as the position of the impinging microwaves changes relative to the irregularity; and
   (b) inferring the depth of the irregularity in the material from the wavelength of the sinusoidal pattern.

7. A method as recited in claim 1, wherein the dielectric material comprises a bulk dielectric containing isolated inclusions of a conductive material.

8. An apparatus for detecting the presence of an irregularity in a bulk dielectric material, comprising:
   (a) a generator of microwaves that are of substantially constant frequency, between 5 and 50 gigahertz; wherein said generator is adapted to direct a first portion of the generated microwaves to impinge onto the material; whereby the impinging microwaves are partially transmitted and partially reflected when the impinging microwaves impinge on an irregularity within the material that is characterized by at least one interface between different dielectric constants; whereby the wavelength of the reflected microwaves is substantially the same as the wavelength of the impinging microwaves; and wherein the reflected microwaves may have an amplitude that differs from the amplitude of the impinging microwaves, or the reflected microwaves may have a phase that differs from the phase of the impinging microwaves, or both;

(b) a mixer to add the reflected microwaves with a second portion of the generated microwaves to produce an interference pattern that is a function of the position, size, shape, and composition of any irregularities in the material; and (c) a computer programmed to infer, from the interference pattern, the position of at least one interface between different dielectric constants in a bulk dielectric material.

9. An apparatus as recited in claim 8, wherein:

(a) said microwave generator is adapted to impinge microwaves onto the material at a plurality of different positions relative to the surface of the material; wherein the direction of the impinging microwaves in at least some of the positions is other than normal to the surface of the material; whereby the interference pattern that is attributable to an irregularity in the material changes in a sinusoidal or attenuated sinusoidal pattern as the position of the impinging microwaves changes relative to the irregularity, wherein the spatial wavelength of the sinusoidal pattern is a function of the angle between the direction of the impinging microwaves and a direction normal to the surface of the material; and (b) said computer is programmed to distinguish features in the interference pattern attributable to irregularities in the material from features in the interference pattern attributable to sources of noise.

10. An apparatus as recited in claim 9, additionally comprising a filter to remove from the interference pattern any features that do not have a sinusoidal or attenuated sinusoidal pattern with a wavelength substantially equal to the wavelength that is characteristic of the angle between the direction of the impinging microwaves and a direction normal to the surface of the material; whereby the signal-to-noise ratio of the interference pattern is enhanced.

11. An apparatus as recited in claim 10, wherein said filter acts by performing a Fourier transform of the interference pattern, and rejecting components of the Fourier transform that do not correspond to a wavelength substantially equal to the wavelength that is characteristic of the angle between the direction of the impinging microwaves and a direction normal to the surface of the material.

12. An apparatus as recited in claim 11, wherein said computer is additionally programmed to generate the first derivative of the Fourier transform with respect to time or displacement, whereby the first derivative enhances the signal-to-noise ratio of the inferred information concerning the position of irregularities in the material.

13. An apparatus as recited in claim 8, wherein:

(a) said microwave generator is adapted to impinge microwaves onto the material at a plurality of different positions relative to the surface of the material; wherein the microwaves impinged onto the material have a substantially spherical wavefront; whereby the interference pattern that is attributable to an irregularity in the material changes in a sinusoidal or attenuated sinusoidal pattern as the position of the impinging microwaves changes relative to the irregularity; and (b) said computer is programmed to infer the depth of the irregularity in the material from the wavelength of the sinusoidal pattern.

* * * * *